United States Patent [19]

Kleiner et al.

[11] Patent Number: 6,013,707
[45] Date of Patent: Jan. 11, 2000

[54] FLAMEPROOFED POLYESTER MOLDING COMPOSITIONS

[75] Inventors: Hans-Jerg Kleiner, Kronberg; Winfried Budzinsky; Günther Kirsch, both of Bad Soden, all of Germany

[73] Assignee: Ticona GmbH, Germany

[21] Appl. No.: 09/094,278

[22] Filed: Jun. 9, 1998

Related U.S. Application Data

[63] Continuation of application No. 08/780,345, Jan. 8, 1997, Pat. No. 5,780,534, which is a continuation of application No. 08/520,728, Aug. 29, 1995, abandoned.

[30] Foreign Application Priority Data

Aug. 31, 1994 [DE] Germany .............................. 44 30 932

[51] Int. Cl.⁷ .................................................. C08K 5/5313
[52] U.S. Cl. .............................................................. 524/126
[58] Field of Search .................................... 524/126, 133, 524/135

[56] References Cited

U.S. PATENT DOCUMENTS

| | | | |
|---|---|---|---|
| 3,594,347 | 7/1971 | Lazarus et al. | 260/45.75 |
| 3,900,444 | 8/1975 | Racky et al. | 260/45.75 |
| 3,953,539 | 4/1976 | Kawase et al. | 260/860 |
| 4,036,811 | 7/1977 | Noetzel et al. | 260/45.75 |
| 4,049,612 | 9/1977 | Sandler et al. | 260/31.8 |
| 4,078,016 | 3/1978 | Kramer et al. | 260/860 |
| 4,180,495 | 12/1979 | Sandler et al. | 260/45.75 |
| 4,208,321 | 6/1980 | Sandler et al. | 260/45.75 |
| 4,208,322 | 6/1980 | Sandler et al. | 260/45.75 |

FOREIGN PATENT DOCUMENTS

| | | |
|---|---|---|
| 0 006 568 | 1/1980 | European Pat. Off. . |
| 2 204 659 | 5/1974 | France . |
| 2 422 698 | 11/1979 | France . |
| 2 102 841 | 8/1971 | Germany . |
| 2 827 867 | 1/1980 | Germany . |
| 51-047035 | 4/1976 | Japan . |

OTHER PUBLICATIONS

B.P. Block, "Polymeric Metal Phosphinates", Inorg. Macromol. Rev., 1 (1970) pp. 115–125.
Chemical Abstracts, vol. 85, No. 10, Sep. 6, 1976 Abstract No. 64058.

*Primary Examiner*—Veronica P. Hoke
*Attorney, Agent, or Firm*—Connolly Bove Lodge & Hutz LLP

[57] ABSTRACT

Polyesters such as polyethylene terephthalate or polybutylene terephthalate are provided with a flame-retardant finish by addition of calcium salts or aluminum salts of phosphinic or diphosphinic acids.

18 Claims, No Drawings

FLAMEPROOFED POLYESTER MOLDING COMPOSITIONS

This is a continuation of Ser. No. 08/780,345 filed Jan. 8, 1997 which is allowed, now U.S. Pat. No. 5,780,534, which is a continuation of Ser. No. 08/520,728, filed Aug. 29, 1995 which is now abandoned.

The invention relates to flameproofed polyester molding compositions which comprise calcium phosphinates or aluminum phosphinates.

Polymers are often rendered flame-resistant by adding to these phosphorus-containing or halogen-containing compounds or mixtures thereof. Some polymers are processed at high temperatures, for example at 250° C. or higher temperatures. For this reason, many known flame retardants are not suitable for such uses, because they are too volatile or are not sufficiently heat-stable.

Alkali metal salts of phosphinic acids are stable to heat and have already been proposed as flame-retardant additives for polyesters (DE-A1-2 252 258). They must be incorporated in amounts of up to 30% by weight, and sometimes have an adverse corrosion-promoting effect on the processing machines.

Salts of phosphinic acids with an alkali metal or a metal of main group or sub-group 2 or 3 of the periodic table have furthermore been employed for the preparation of flame-resistant polyamide molding compositions, in particular the zinc salts (DE-A1-2 447 727). Thermoplastics of low flammability can also be prepared by using the phosphinic acid salts mentioned in combination with nitrogen bases, such as melamine, dicyandiamide or guanidine (DE-A1-28 27 867).

The polymeric metal phosphinates are another large class of phosphinic acid salts. These are nonionic co-ordination complexes and are soluble in organic solvents. They are suitable as flameproofing components for halogenated aromatic polymers and for polyesters (U.S. Pat. No. 4,078,016; U.S. Pat. No. 4,180,495), polyamides (U.S. Pat. No. 4,208,321) and polyester/polyamides (U.S. Pat. No. 4,208,322). The generally difficult industrial preparation of these metal phosphinate polymers is a disadvantage.

It has now been found, surprisingly, that calcium salts and aluminum salts of phosphinic or diphosphinic acids display an excellent flame-retardant action in polyester plastics, while other metal salts of the same phosphinic or diphosphinic acids result in a considerably poorer flame-retardant action.

The invention thus relates to a polyester molding composition which comprises a phosphinic acid salt of the formula (I) and/or a diphosphinic acid salt of the formula (II) and/or polymers thereof

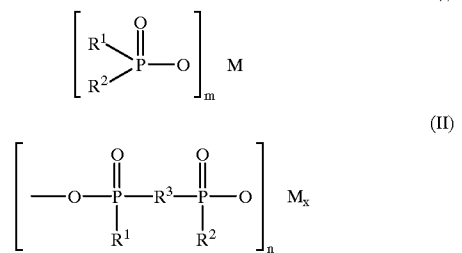

in which
 $R^1$ and $R^2$ are $C_1$–$C_6$-alkyl, preferably $C_1$–$C_4$-alkyl, which is linear or branched, for example methyl, ethyl, n-propyl, iso-propyl, n-butyl, tert-butyl or n-pentyl; or phenyl;

$R^3$ is $C_1$–$C_{10}$-alkylene which is linear or branched, for example methylene, ethylene, n-propylene, iso-propylene, n-butylene, tert-butylene, n-pentylene, n-octylene or n-dodecylene; arylene, for example phenylene or naphthylene; alkylarylene, for example methylphenylene, ethylphenylene, tert-butylphenylene, methylnaphthylene, ethylnaphthylene or tort-butylnaphthylene; arylalkylene, for a-ample phenylmethylene, phenylethylene, phenylpropylene or phenylbutylene;
 M is calcium or aluminum ions;
 m is 2 or 3;
 n is 1 or 3; and
 x is 1 or 2.

Polyesters are polymers which contain recurring units bonded via an ester group in the polymer chain. Polyesters which can be employed according to the invention are described, for example, in "Ullmann's Encyclopedia of Industrial Chemistry, ed. Barbara Elvers, Volume A21, Chapter "Polyesters" (pages 227–251), VC, Weinheim-Basel-Cambridge-New York 1992", to which reference is made.

The term "phosphinic acid salt" below means salts of phosphinic and diphosphinic acids and polymers thereof.

The phosphinic acid salts according to the invention, which are prepared in an aqueous medium, are in general monomeric compounds. Polymeric phosphinic acid salts can also be formed under certain circumstances, depending on the preparation conditions.

Suitable phosphinic acids as a constituent of the phosphinic acid salts according to the invention are, for example: dimethylphosphinic acid, ethylmethylphosphinic acid, diethylphosphinic acid, methyl-n-propylphosphinic acid, methane-di(methylphosphinic acid), ethane-1,2-di(methylphosphinic acid), hexane-1,6-di(methylphosphinic acid), benzene-1,4-di(methylphosphinic acid), methylphenylphosphinic acid and diphenylphosphinic acid.

The salts of the phosphinic acids according to the invention can be prepared by known methods. The phosphinic acids are reacted here with metal carbonates, metal hydroxides or metal oxides in aqueous solution.

The amount of phosphinic acid salt of the formula I to be added to the polymers or of the diphosphinic acid salt of the formula II can vary within wide limits. In general, 5 to 30% by weight, based on the polymer, is used. The optimum amount depends on the nature of the polymer and on the nature of the phosphinic acid salt employed, and can easily be determined by experiments.

The phosphinic acid salts according to the invention can be used in various physical forms, depending on the nature of the polymer used and on the desired properties. Thus, for example, the phosphinic acid salts can be ground to a finely divided form in order to achieve a better dispersion in the polymer. If desired, mixtures of different phosphinic acid salts can also be employed.

The phosphinic acid salts according to the invention are heat-stable and neither decompose the polymers during processing nor influence the preparation process of the polyester molding composition. The phosphinic acid salts are not volatile under the preparation and processing conditions for polymers.

The phosphinic acid salt can be incorporated into the polymer by mixing the two, subsequently melting the polymer in a compounding unit (for example a twin-screw extruder) and homogenizing the phosphinic acid salt in the polymer melt. The melt can be taken off as a strand, cooled and granulated. The phosphinic acid salt can also be metered directly into the compounding unit.

It is also possible to admix the flame retardant additives to finished polyester granules and to process the mixture directly on an injection molding machine, or to melt it beforehand in an extruder, granulate it and process it after a drying process.

The flame-retardant additive can also be added during the polycondensation.

In addition to the phosphinic acid salts according to the invention, fillers and reinforcing substances, such as glass fibers, glass beads or minerals, such as chalk, can also be added to the formulations. In addition, the products can comprise other additives, such as, for example, stabilizers, lubricants, colorants, nucleating agents or antistatics.

The flame-resistant polyesters according to the invention are suitable for the production of shaped articles, films, filaments and fibers, for example by injection molding, extrusion or compression molding.

EXAMPLES

1. Preparation of Phosphinic Acid Salts 1.1 Preparation of the Calcium Salt of Ethylmethylphosphinic Acid 1630 g (15.1 mol) of ethylmethylphosphinic acid are dissolved in 3 l of water and 422.8 g (7.55 mol) of calcium oxide (unslaked lime) are introduced in portions in the course of 1.5 hours, while stirring vigorously, the temperature rising to 75° C. Further calcium oxide is then introduced until a pH electrode introduced into the solution indicates pH=7. A little active charcoal is then added and the mixture is stirred under reflux for 1.5 hours and then filtered. The filtrate is evaporated to dryness and dried to constant weight in a vacuum drying cabinet at 120° C. 1920 g of a white powder which does not melt at up to 300° C. are obtained. Yield: 100% of theory.

1.2 Preparation of the Aluminum Salt of Ethylmethylphosphinic Acid 2106 g (19.5 mol) of ethylmethylphosphinic acid are dissolved in 6.5 l of water and 507 g (6.5 mol) of aluminum hydroxide are added, while stirring vigorously, the mixture being heated to 85° C. The mixture is stirred at 80–90° C. for 65 hours in total and is then cooled to 60° C. and filtered with suction. After drying to constant weight in a vacuum drying cabinet at 120° C., 2140 g of a fine-grained powder which does not melt at up to 300° C. are obtained. Yield: 95% of theory.

1.3 Preparation of the Calcium Salt of Ethane-1,2-bismethylphosphinic Acid 325.5 g (1.75 mol) of ethane-1,2-bismethylphosphinic acid are dissolved in 500 ml of water and 129.5 g (1.75 mol) of calcium hydroxide are introduced in portions in the course of one hour, while stirring vigorously. The mixture is then stirred at 90–95° C. for a few hours, cooled and filtered with suction. After drying in a vacuum drying cabinet at 150° C., 335 g are obtained. The product does not melt at up to 380° C. Yield: 85% of theory.

1.4 Preparation of the Aluminum Salt of Ethane-1,2-bismethylphosphinic Acid 334.8 g (1.8 mol) of ethane-1,2-bismethylphosphinic acid are dissolved in 600 ml of water and 93.6 g (1.2 mol) of aluminum hydroxide are introduced in portions in the course of one hour, while stirring vigorously. The mixture is then kept under reflux for 24 hours and subsequently filtered hot with suction, and the product is washed with water. After drying, 364 g of a white powder which does not melt at up to 380° C. are obtained. Yield: 100% of theory.

1.5 Preparation of the Calcium Salt of Methylpropylphosphinic Acid 366 g (3.0 mol) of methylpropylphosphinic acid are dissolved in 600 ml of water and 84 g (1.5 mol) of calcium oxide are introduced in portions, while stirring vigorously, the temperature thereby rising to 65° C. The mixture is now kept at this temperature until a clear solution has formed. It is now evaporated to dryness in vacuo. After the residue has been dried at 120° C. in a vacuum drying cabinet, 364 g are obtained. Yield: about 85% of theory.

2. Preparation and Testing of Flame-retardant Polyesters

The phosphorus-containing compounds were mixed with the polymer and incorporated on a commercially available twin-shaft compounder. In the case of glass-fiber-reinforced formulations, glass fibers which are commercially conventional for polyesters were metered into the melt.

The material temperatures during compounding were about 250° C. for polybutylene terephthalate (PBT) and about 270° C. for polyethylene terephthalate (PET).

The test specimens were produced on an injection molding machine in accordance with ISO 7792-2.

The fire class UL 94 (Underwriter Laboratories) was determined on test specimens from each mixture which had a thickness of 1.2 mm, and the tear strength and elongation at break were determined in accordance with ISO 527.

The following fire classes result according to UL 94:

V-0 no afterflaming for longer th an 10 seconds, total of the afterflame times of 10 flamings not greater than 50 seconds, no burning drops, no complete burnup of the specimen, no afterglowing of the specimens for longer than 30 seconds after the end of flaming V-1 no afterflaming for longer than 30 seconds after the end of flaming, total of the afterflame times of 10 flamings not greater than 250 seconds, no afterglowing of the specimens for longer than 60 seconds after the end of flaming, other criteria as for V-0

V-2 ignition of the cottonwool pad by burning drops, other criteria as for V-1

<V-2 does not comply with fire class V-2.

2.1.1 Compounds reinforced with 30% of glass fibers and without further additives were prepared from PBT and the calcium salt of ethylmethyiphosphinic acid in various concentrations, and were injection-molded to give test specimens and tested with the following result:

| Concentration of Ca salt/% | Fire class UL 94 | Tear strength/ N mm$^2$ | Elongation at break/% |
|---|---|---|---|
| 20 | V-0 | 130 | 2.4 |
| 17.5 | V-0 | 134 | 2.7 |
| 15 | V-2 | 139 | 3.0 |
| 12.5 | <V-2 | 140 | 3.1 |

2.1.2 Correspondingly with the calcium salt of propylmethylphosphinic acid (polymer: PBT):

| Concentration of Ca salt % | Fire class UL 94 V-0 | Tear strength N/mm$^2$ | Elongation at break % |
|---|---|---|---|
| 20 | V-0 | 133 | 2.2 |

2.2 The procedure was as for Example 2.1.1 with the aluminum salt of ethylmethylphosphinic acid (polymer:

| Concentration of Al salt % | Fire class UL 94 | Tear strength N/mm² | Elongation at break % |
|---|---|---|---|
| 20 | V-0 | 115 | 2.0 |
| 17.5 | V-1 | 120 | 1.9 |
| 15 | V-2 | 130 | 2.1 |
| 12.5 | V-2 | 135 | 2.5 |

On addition of 20% of the phosphorus-containing compound, fire class UL 94 V-0 is established, while only UL 94 V-1 is reached with 17.5%.

2.3 (Comparison Example)

The influence of the sodium salt of ethylmethylphosphinic acid, mentioned in the German Application DE-A1-2 252 258, on flame resistance of PBT is shown:

| Concentration of Na salt % | Fire class UL 94 | Tear strength N/mm² | Elongation at break % |
|---|---|---|---|
| 30 | V-0 | 40 | 0.4 |
| 20 | <V-2 | 70 | 1.0 |
| 15 | <V-2 | 93 | 1.5 |
| 10 | <V-2 | 116 | 1.7 |

30% of this compound is necessary to achieve UL 94 V-0; at a concentration of 20%, fire class UL 94 V-2 is no longer met. The flame-retardant action of this compound is considerably lower than that of the compounds according to the invention mentioned in Examples 1 and 2. In addition, very low tear strength and elongations at break values of the injection-molded test specimens result in comparison with the formulations with the compounds according to the invention, and these values are not acceptable in practice.

2.4 Examples with glass-fiber-reinforced PBT have been given so far. Example 2.4 shows the activity of the compounds claimed in nonreinforced PBT using the example of the calcium salt of ethylmethylphosphinic acid.

|  | Concentration of Ca salt/% | Fire class UL 94 |
|---|---|---|
| Nonreinforced | 25 | V-0 |
| Nonreinforced | 20 | V-1 |

It is necessary to employ a higher amount for nonreinforced products compared with glass-fiber-reinforced formulations, in which the polymer content is lower.

2.5 Example 2.5 shows the activity of the compounds claimed in nonreinforced and reinforced PET using the example of the calcium salt of ethylmethylphosphinic acid.

|  | Concentration of Ca salt % | Fire class UL 94 |
|---|---|---|
| Nonreinforced | 25 | V-0 |
| 30% of glass fibers | 30 | V-0 |
| 30% of glass fibers | 25 | V-0 |
| 30% of glass fibers | 20 | V-0 |

We claim:

1. A polyester molding composition comprising a diphosphinic acid salt of the formula (II) or a mixture of the phosphinic acid salt of the formula (I) and diphosphinic acid salt of the formula (II)

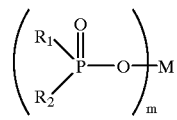

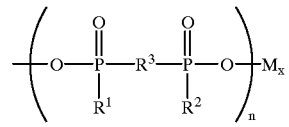

wherein
$R^1$ and $R^2$ are identical or different and represent $C_1$–$C_4$-alkyl, which is linear or branched;
$R^3$ is a $C_1$–$C_{10}$ alklylene, which is linear or branched; arylene; alkylarylene; or arylalkylene;
M represents calcium ion or aluminum ion;
m is 2 or 3;
n is 1 or 3;
x is 1 or 2,
in a flame retardant amount.

2. The polyester molding composition as claimed in claim 1, comprising polybutylene terephthalate as the polyester.

3. The polyester molding composition as claimed in claim 1, comprising polyethylene terephthalate as the polyester.

4. The polyester molding composition as claimed in claim 1, comprising a calcium salt of at least one phosphinic acid of the formula I.

5. The polyester molding composition as claimed in claim 1, comprising a calcium salt of at least one phosphinic acid of the formula II.

6. The polyester molding composition as claimed in claim 1, comprising an aluminum salt of at least one pbosphinic acid of the formula I.

7. The polyester molding composition as claimed in claim 1, comprising an aluminum salt of at least one phosphinic acid of the formula II.

8. The polyester molding composition as claimed in claim 1, comprising about 5 to 30% by weight of a phosphinic acid salt of the formula I, calculated on total weight of the polyester molding composition.

9. The polyester molding composition as claimed in claim 1, comprising about 5 to 30% by weight of a phosphinic acid salt of the formula II, calculated on total weight of the polyester molding composition.

10. The polyester molding composition as claimed in claim 1, comprising about 5 to 30% by weight of a mixture of a phosphinic acid salt of the formula I and of a diphosphinic acid salt of the formula II, calculated on total weight of the polyester molding composition.

11. The polyester molding composition as claimed in claim 1, comprising about 5 to 30% by weight of a polymer of phosphinic acid salt of the formula II, calculated on total weight of the polyester molding composition.

12. The polyester molding composition as claimed in claim 1, comprising about 5 to 30% by weight of a mixture of a polymer of phosphinic acid salt of the formula I and of a polymer of diphosphinic acid salt of the formula II, calculated on total weight of the polyester molding composition.

13. The polyester molding composition as claimed in claim 1, comprising about 5 to 30% by weight of a mixture of a phosphinic acid salt of the formula I and of a diphosphinic acid salt of the formula II and of a polymer thereof, calculated on total weight of the polyester molding composition.

14. A method for the preparation of a flamed proof polyester molding composition comprising a step of adding a flame retardant amount of a diphosphinic acid salt of the formula (II) or a mixture of the phosphinic acid salt of the formula (I) and diphosphinic acid salt of the formula (II)

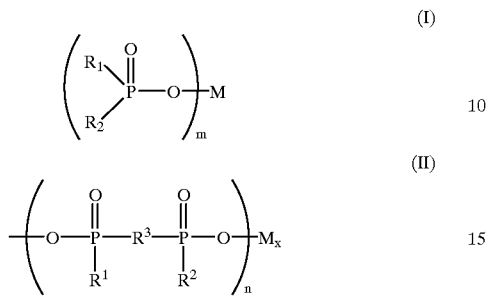

wherein
$R^1$ and $R^2$ are identical or different and represent $C_1$–$C_4$-alkyl, which is linear or branched;
$R^3$ is a $C_1$–$C_{10}$ alklylene, which is linear or branched; arylene; alkylarylene; or arylalkylene;
M represents calcium ion or aluminum ion;
m is 2 or 3;
n is 1 or 3;
x is 1 or 2.

15. The method as claimed in claim 14, wherein the polyester is a polyethylene terephthalate.

16. The method as claimed in claim 14, wherein the polyester is a polybutylene terephthalate.

17. A polyester molding composition comprising a water insoluble diphosphinic acid salt of the formula (II)

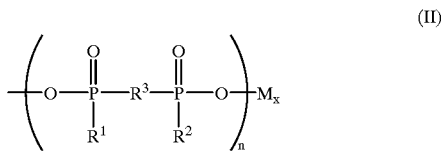

wherein
$R^1$ and $R^2$ are identical or different and represent $C_1$–$C_4$-alkyl, which is linear or branched;
$R^3$ is a $C_1$–$C_{10}$ alklylene, which is linear or branched; arylene; alkylarylene; or arylalkylene;
M represents calcium ion or aluminum ion;
n is 1 or 3;
x is 1 or 2,
in a flame retardant amount.

18. The method as claimed in claim 14, wherein a water insoluble diphosphinic acid salt of the formula (II) is used in said step of adding.

* * * * *